United States Patent [19]

Beck et al.

[11] 4,067,721
[45] Jan. 10, 1978

[54] IMIDAZOLIDINEDIONE COMPOUNDS AND PLANT GROWTH INFLUENCING COMPOSITIONS

[75] Inventors: Gunther Beck; Helmut Heitzer, both of Leverkusen; Klaus Lürssen, Berg. Gladbach, all of Germany

[73] Assignee: Bayer Aktiengesellschaft, Leverkusen, Germany

[21] Appl. No.: 734,230

[22] Filed: Oct. 20, 1976

[30] Foreign Application Priority Data

Nov. 7, 1975 Germany .............................. 2550157

[51] Int. Cl.² ...................... A01N 9/22; C07D 233/02
[52] U.S. Cl. ......................................... 71/92; 548/307; 548/337
[58] Field of Search ........................... 260/309.7; 71/92

[56] References Cited
U.S. PATENT DOCUMENTS

| | | | |
|---|---|---|---|
| 3,384,643 | 5/1968 | Sayigh et al. | 260/309.7 |
| 3,389,146 | 6/1968 | Kitasaki et al. | 71/92 X |
| 3,748,356 | 7/1973 | Wellinga et al. | 260/309.7 |
| 3,843,677 | 10/1974 | Cleveland | 71/92 |

Primary Examiner—Joseph Paul Brust
Attorney, Agent, or Firm—Burgess, Dinklage & Sprung

[57] ABSTRACT

New imidazolidinedione compounds of the formula

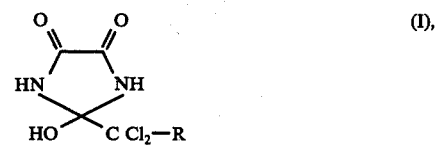

in which
R is chlorine, alkyl of 1 or 2 carbon atoms or chloroalkyl of 1 or 2 carbon atoms and 1 to 5 chlorine atoms are outstandingly effective as plant growth regulants and have surprisingly been found to exhibit substantially greater activity than conventional materials of this type.

14 Claims, No Drawings

IMIDAZOLIDINEDIONE COMPOUNDS AND PLANT GROWTH INFLUENCING COMPOSITIONS

The present invention relates to certain new imidazolidinedione compounds, to plant growth regulant compositions containing them and to their use for influencing plant growth.

It is known that (2-chloroethyl)-trimethylammonium chloride exhibits plant growth-regulating properties (See U.S. Pat. No. 3,156,554). However, the activity of this compound is not always entirely satisfactory, especially if low amounts are used. Further, it is known that a product commercially available under the name "Off-Shoot-T", based on fatty alcohols with 6, 8, 10 and 12 carbon atoms, can be employed for regulating plant growth, especially for suppressing the growth of side shoots of tobacco (see Farm. Chem. Handbook, 1975, Meister Publishing Co., Willoughby, Ohio 1975, Pesticide Dictionary D 147).

However, in some cases, especially if low amounts are used, the activity of this product also leaves something to be desired.

The present invention provides, as new compounds, the imidazolidinedione derivatives of the general formula

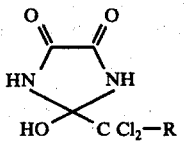

in which
R is chlorine, alkyl of 1 or 2 carbon atoms or chloroalkyl of 1 or 2 carbon atoms and 1 to 5 chlorine atoms.

The present compounds exhibit strong plant growth-regulating properties.

Preferably, R represents chlorine, methyl, chloromethyl, dichloromethyl or trichloromethyl.

The present invention also provides a process for the preparation of an imidazolidinedione derivative of the formula (I) in which a chlorinated imidazole derivative of the general formula

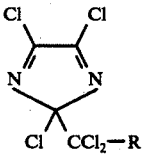

in which
R has the abovementioned meaning,
is reacted with a hydrolysing agent.

Surprisingly, the imidazolidinedione derivatives of the formula (I), according to the invention, exhibit a substantially greater plant growth-regulating action than (2-chloroethyl)-trimethylammonium chloride, known from the state of the art, and than the product "Off-Shoot-T", which is also known, these being compounds of the same type of action and recognized to have a good activity. The compounds according to the invention thus represent a valuable enrichment of the art.

If 2,4,5-trichloro-2-trichloromethyl-2H-imidazole and formic acid are used as starting materials, the course of the reaction can be represented by the following equation:

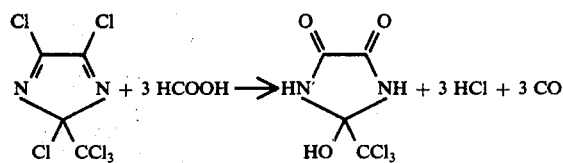

The chlorinated imidazole derivatives of the formula (II) which can be used according to the invention have not previously been described in the literature. However, they can be prepared by converting 2-alkyl-imidazoles of the general formula

in which
$R^1$ represents alkyl with 1 to 3 carbon atoms,
to the corresponding hydrochlorides by reaction with hydrogen chloride in an inert diluent at room temperature, and then reacting these, without prior isolation, with elementary chlorine, first at room temperature and then whilst gradually raising the temperature to 50°–150° C.

Diluents which can be employed in the preparation of the compounds of the formula (II) are in principle all inert solvents which are resistant to chlorine. These include, in particular, phosphorus oxychloride, chloroform and 1,1,2,2-tetrachloroethane.

In preparing the compounds of the formula (II) the procedure generally followed is, in detail, that hydrogen chloride gas is passed into a solution or suspension of a compound of the formula (III) in an inert diluent at room temperature, while cooling, and a reaction is then carried out with elementary chlorine, initially at room temperature. To achieve as rapid and complete conversion as possible, the amount of chlorine used is always so chosen, during the entire course of the chlorination, that a greenish coloration of the off-gas indicates a slight excess. The reaction mixture, which is initially at room temperature, is gradually warmed to a temperature of 50° to 150° C, in the course of which it is advantageous always only to raise the temperature when an exothermic phase has subsided. The particular final temperature depends on the diluent used. If, for example, phosphorus oxychloride or chloroform is employed, a temperature near the lower limit of the stated temperature range is used. If, on the other hand, 1,1,2,2-tetrachloroethane is used as the diluent, a temperature near the upper limit of the stated temperature range is used.

Of course, chlorinations in phosphorus oxychloride or chloroform can also be carried out above the reflux temperature of the particular diluent, by stripping off the solvent under reduced pressure and continuing the chlorination up to the desired temperature, or by distilling off the diluent, in a stream of chlorine, in the course of raising the temperature. After completion of the chlorination, the reaction products are isolated by first stripping off the diluent and then either distilling the residue which remains under reduced pressure and recrystallising the product if appropriate, or directly recrystallising the product, without prior distillation, from a suitable solvent.

The following may be mentioned as individual examples of the compounds of the formula (II) which can be used according to the invention: 2,4,5-trichloro-2-trichloromethyl-2H-imidazole, 2,4,5-trichloro-2-(1,1-dichloroethyl)-2H-imidazole, 2,4,5-trichloro-2-(1,1-dichloropropyl)-2Himidazole, 2,4,5-trichloro-2-(1,1,2-trichloroethyl)-2H-imidazole, 2,4,5-trichloro-2-(1,1,2,2-tetrachloroethyl)-2H-Imidazole and 2,4,5-trichloro-2-(1,1,2,2,2-pentachloroethyl)-2H-imidazole.

In carrying out the process according to the invention for the preparation of the new imidazolidinedione derivatives of the formula (I), suitable hydrolyzing agents are strong inorganic or organic acids. The following may be mentioned as being preferred: concentrated sulphuric acid, concentrated phosphoric acid and formic acid.

The process according to the invention for the preparation of the new imidazolidinedione derivatives of the formula (I) is in general carried out in the absence of additional solvents or diluents. However, in principle it is also possible to carry out the reaction according to the invention in the presence of an inert diluent, such as, for example, tetrahydrofuran or dioxan.

The reaction temperatures can be varied within a fairly wide range. In general, the reaction is carried out at between $-20°$ and $+120°$ C, preferably between $0°$ and $50°$ C.

In general, the process according to the invention is carried out under normal pressure.

In carrying out the process according to the invention, it is advantageous to employ at least 3 moles of the hydrolyzing agent per mole of starting compound of the formula (II). Advantageously, the hydrolyzing agent at the same time serves as the reaction medium. Hence, up to 10 parts by weight of hydrolyzing agent are generally employed per part by weight of starting compound of the formula (II).

In the preparation of the new imidazolidinedione derivatives according to the process of the invention, the reaction products, after completion of the reaction, are either obtained directly in a crystalline form or can be separated out in the crystalline state by adding water, in which they are practically insoluble. The crystalline products are isolated by simple suction filtration. An additional purification is in general not required but can, if necessary, be carried out in accordance with customary processes, for example by recrystallization ation from organic solvents, such as acetonitrile.

The following may be mentioned as individual examples of the imidazolidinedione derivatives of the formula (I), according to the invention: 2-hydroxy-2-trichloromethylimidazolidine-4,5-dione, 2-hydroxy-2-(1,1-dichloroethyl)-imidazolidine-4,5-dione, 2-hydroxy-2-(1,1-dichloropropyl)-imidazolidine-4,5-dione, 2-hydroxy-2-(1,1,2-trichloroethyl)-imidazolidine-4,5-dione, 2-hydroxy-2-(1,1,2,2-tetrachloroethyl)-imidazolidine-4,5-dione and 2-hydroxy-2-(1,1,2,2,2-pentachloroethyl)-imidazolidine-4,5-dione.

The active compounds according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended favorably to influence the crop plants in the desired manner.

Plant growth-regulating compounds can be employed, for example to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which again counteracts lodging.

In the case of many crop plants, inhibition of the vegetative growth permits denser planting of the crop, so that a greater yield per area of ground can be achieved. A further mechanism of increasing the yield by means of growth inhibitors is based on the fact that the nutrients benefit blossoming and fruit formation to a greater extent, while vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about a better quality of the harvested products. Thus it is possible, for example, to increase the content of sugar in sugar beet, sugar cane, pineapple and citrus fruits or to increase the protein content in soya or cereals.

Parthenocarpous fruit can be formed under the influence of growth regulators. Furthermore, the gender of the flowers can be influenced.

Using growth regulators it is also possible to favorably influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defolation of the plants at a desired point in time is achieved. Such defoliation is of interest in order to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can in some cases improve the coloration of fruit. In addition, concentrating the ripening within a certain period of time is also achievable with the aid of growth regulators. This provides the preconditions for being able to carry out completely mechanical or manual harvesting in only a single pass, for example on the case of tobacco, tomatoes or coffee.

By using growth regulators it is also possible to influence the latent period of seeds or buds of plants, that is to say the endogenic annual rhythm, so that the plants, such as, for example, pineapple or ornamental plants in nurseries, germinate, shoot or blossom at a time at which they normally show no readiness to do so.

Using growth regulators it is also possible to achieve a delay in the shooting of buds or the germination of seeds, for example in order to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xyelens, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty /acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds, such as fungicides, insecticides, acaricides and herbicides, as well as mixed with fertilisers.

The formulations in general contain from 0.1 to 95% by weight of active compound, preferably from 0.5 to 90% by weight.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming, gassing and the like. It is furthermore possible to apply the active compounds by the ultra-low-volume process, to brush plants or parts of plants with the active compound preparation or the active compound itself, or inject the active compound preparation, or the active compound itself, into the soil. The seed of the plants can also be treated.

The amount of active compound employed can vary within substantial ranges. In general, from 0.01 to 50 kg, preferably from 0.05 to 10 kg, of active compound are used per hectare of soil surface.

The preferred space of time within which the growth regulators are used depends on the climatic and vegetative circumstances.

The present invention also provides plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants or to a habitat thereof, a compound of the present invention alone or in the form of a composition containing as active ingredient a compound of the present invention in admixture with a diluent or carrier.

The present invention further provides means of yielding plants, the growth of which has been regulated by their being grown in areas in which immediately prior to and/or during the time of the growing, a compound of the present invention was applied alone or in admixture with a diluent or carrier.

It will be seen that the usual methods of providing a harvested crop may be improved by the present invention.

The plant-growth-regulating activity of the compounds of this invention is illustrated by the following biotest Examples.

EXAMPLE A

Inhibition of growth/wheat

Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young wheat plants in the two-leaf stage were sprayed with the preparation of active compound until dripping wet. After the untreated control plants had grown to a height of about 60 cm, the additional growth was measured on all plants and the inhibition of growth in % of the additional growth of the control plants was calculated. 100 % means that growth had stopped and 0% denotes a growth corresponding to that of the control plants.

The active compounds, active compound concentrations and results can be seen from the table which follows.

Table A

| Active compound | Inhibition of growth/wheat Active compound concentration in % | Inhibition of growth in % |
|---|---|---|
| — (Control) | — | 0 |
| Cl—CH$_2$—CH$_2$—N$^\oplus$(CH$_3$)$_3$ Cl$^\ominus$ (known) | 0.05 | 50 |
| 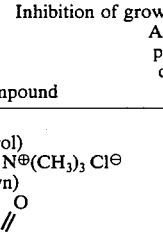 (1) | 0.05 | 55 |
| 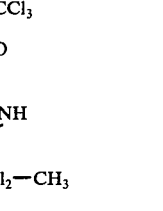 (2) | 0.05 | 80 |

EXAMPLE B

Inhibition of growth/barley

Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young barley plants in the two-leaf stage were sprayed with the preparation of active compound until dripping wet. After the untreated control plants had grown to a height of about 60 cm, the additional growth was measured on all plants and the inhibition of growth in % of the additional growth of the control plants was calculated. 100% means that growth had stopped and 0% denotes a growth corresponding to that of the control plants.

The active compounds, active compound concentrations and results can be seen from the table which follows.

Table B

| Active compound | Inhibition of growth/barley Active compound concentration in % | Inhibition of growth in % |
|---|---|---|
| — (Control) | — | 0 |
| Cl—CH$_2$—CH$_2$—N$^\oplus$(CH$_3$)$_3$Cl$^\ominus$ (known) | 0.05 | 20 |
| 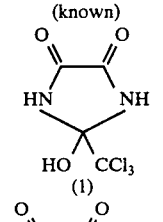 (1) | 0.05 | 50 |
| 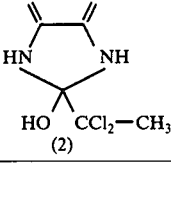 (2) | 0.05 | 55 |

EXAMPLE C

Inhibition of growth/soya beans

Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

Young soya bean plants, in the stage in which the first secondary leaves had unfolded, were sprayed with the preparation of active compound until dripping wet. After 2 weeks, the additional growth was measured and the inhibition of growth in % of the additional growth of the control plants was calculated. 100% means that growth had stopped and 0% denotes a growth corresponding to that of the untreated control plants.

The active compounds, active compound concentration and results can be seen from the table which follows.

Table C

| Active compound | Inhibition of growth/soya beans Active compound concentration in % | Inhibition of growth in % |
|---|---|---|
| — (Control) | — | 0 |
| 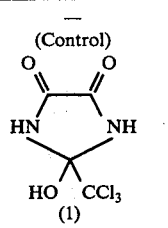 (1) | 0.05 | 50 |

Table C-continued

| Active compound | Inhibition of growth/soya beans Active compound concentration in % | Inhibition of growth in % |
| --- | --- | --- |
| 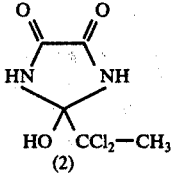 (2) | 0.05 | 50 |

EXAMPLE D

Inhibition of growth of side shoots of tobacco

Solvent: 10 parts by weight of methanol
Emulsifier: 2 parts by weight of polyethylene-sorbitan monolaurate To prepare a suitable preparation of active compound, 1 part by weight of active compound was mixed with the stated amounts of solvent and emulsifier and the mixture was made up to the desired concentration of water.

The shoot tips of about 50 cm high tobacco plants were pinched out. On the following day, plants were sprayed with the preparations of active compound until dripping wet. After 3 weeks the side shoots, which had formed during this time, were pinched out and weighed. The weight of the side shoots of the treated plants were compared with the weight of the side shoots of the untreated control plants and expressed in %. 100% inhibition means that side shoots were absent and 0% means a growth of side shoots which corresponded to that of the control plants.

The active compounds, active compound concentrations and results can be seen from the table which follows:

Table D

| Active compound | Inhibition of growth of side shoots of tobacco Active compound concentration in % | Inhibition of the growth of side shoots in % |
| --- | --- | --- |
| — (Control) | — | 0 |
| "Off-Shoot-T" (known) | 0.2 | 20 |
| 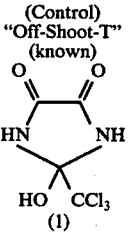 (1) | 0.2 | 60 |

NOTE: "Off-Shoot-T" is a commercially available growth regulator, based on fatty alcohols with 6, 8, 10 and 12 carbon atoms

EXAMPLE E

Effect on growth of woody plants (*Acer pseudoplatanus* and *Alnus glutinosa*)

Solvent: 10 parts by weight of methanol
Emulsifier: 2 parts by weight of polyethylene sorbitan monolaurate To prepare a suitable preparation of active compound, 1 part by weight of active compound was mixed with the stated amounts of solvent and emulsifier and the mixture was made up to the desired concentration with water.

One-year-old seedlings which had grown to a height of about 25 cm were sprayed with the preparation of active compound until dripping wet. After 6 weeks' growth in a greenhouse, the additional growth was measured and the effect on the growth, in % of the additional growth of the control plants, was calculated. 0% denotes a growth which corresponds to that of the control plants. Positive values characterise promotion of growth in comparison to the control plants whereas negative values correspondingly indicate an inhibition of growth.

The active compounds, active compound concentrations and results can be seen from the table which follows.

Table E

| Active compound | Effect on growth of woody plants Active compound concentration in % | Effect on growth in % *Acer pseudoplatanus* | *Alnus glutinosa* |
| --- | --- | --- | --- |
| — (Control) | — | 0 | 0 |
| 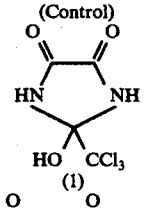 (1) | 0.1 0.2 | −2 −45 | −34 −51 |
| 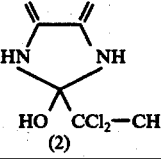 (2) | 0.1 0.2 | +11 +4 | +47 +30 |

The process of the present invention is illustrated by the following preparative Examples.

EXAMPLE 1

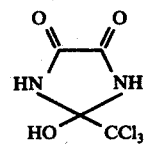 (1)

350 g (1.21 moles) of 2,4,5-trichloro-2-trichloromethyl-2H-imidazole were introduced into 900 g of formic acid over the course of half an hour at a temperature of 10° to 20° C, whilst stirring and cooling with ice. The crystalline precipitate was then filtered off and dried. 245 g (86.5% of theory) of 2-hydroxy-2-trichloromethyl-imidazolidine-4,5-dione of melting point 245° C (from acetonitrile) were thus obtained.

Analysis: ($C_4H_3Cl_3N_2O_3$)— Calculated: 20.6% C; 1.3% H; 45.6% Cl; 12.0% N; 20.5% O. Found: 20.7% C; 1.3% H; 45.9% Cl; 12.0% N; 20.7% O.

A comparatively good yield of 2-hydroxy-2-trichloromethylimidazolidine-4,5-dione was obtained by hydrolysis of 2,4,5-trichloro-2-trichloromethyl-2H-imidazole with concentrated sulphuric acid at 20° C. Working up in this case was carried out by pouring the reaction mixture onto ice-water and filtering off the resulting crystalline precipitate, washing it with water and drying it.

EXAMPLE 2

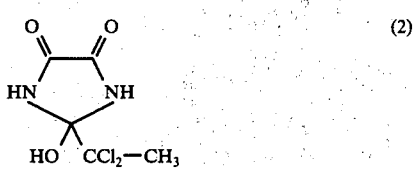
(2)

50 g (0.186 mole) of 2,4,5-trichloro-2-(1,1,-dichloroethyl)-2H-imidazole were introduced, in portions, into 300 g of formic acid at a temperature of 20° to 30° C, while stirring. The amount of the crystals which had separated out was increased by stripping off the excess formic acid under reduced pressure. The residue which remained was recrystallized from acetonitrile. 39 g (98.5% of theory) of 2-hydroxy-2-(1,1-dichloroethyl)-imidazolidine-4,5-dione of melting point 220° C were thus obtained.

The elementary composition $C_5H_6Cl_2N_2O_3$ is confirmed by the mass spectrum.

PREPARATION OF THE STARTING MATERIALS

Example 1a

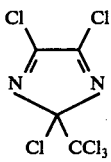

A vigorous stream of hydrogen chloride was passed over a stirred suspension of 750 g (9.15 moles) of 2-methylimidazole in 3,000 ml of phosphorus oxychloride, while initially cooling with ice, until the exothermic reaction of the formation of the hydrochloride had subsided and only a little further hydrogen chloride was absorbed by the suspension (time required, about 1 hour). Chlorine gas was then passed in, starting at room temperature, initially with slight cooling and subsequently with a slow rise in temperature. After a chlorination time of 17 hours, a clear light yellow solution was obtained at 53° C. During a further 6 hours, the mixture was heated in a stream of chlorine until the reflux temperature (about 105° C) was reached. The mixture was post-chlorinated for a further 2 hours at this temperature. It was then worked up by stripping off the phosphorus oxychloride and subjecting the residue to a fractional distillation under reduced pressure. In this way, 2,479 g (93% of theory) of 2,4,5-trichloro-2-trichloromethyl-2H-imidazole were obtained in a purity of 99.0% (determined by gas chromatography).

Boiling point: 96°-105° C at 0.3 mm Hg.

Melting point: 66°-68° C after recrystallization from petroleum ether.

Example 2a

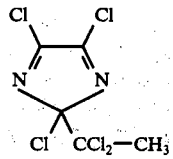

Using the method described in Example 1a, reaction of 2-ethyl-imidazole with hydrogen chloride in phosphorus oxychloride, followed by chlorination of the hydrochloride with elementary chlorine, gave 2,4,5-trichloro-2-(1,1-dichloroethyl)-2H-imidazole in a yield of about 90% of theory.

Melting point: 58°-60° C.

It will be understood that the specification and examples are illustrative but not limitative of the present invention and that other embodiments within the spirit and scope of the invention will suggest themselves to those skilled in the art.

What is claimed is:

1. Imidazolidinedione compound of the formula

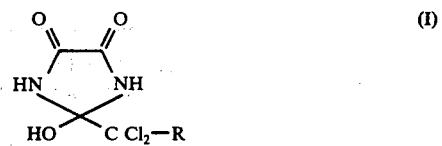
(I)

wherein
R is chlorine, alkyl of from 1 or 2 carbon atoms or chloroalkyl of from 1 or 2 carbon atoms and 1 to 5 chlorine atoms.

2. Imidazolidinedione compound as claimed in claim 1 wherein R is chlorine.

3. Imidazolidinedione compound as claimed im claim 1 wherein R is alkyl.

4. Imidazolidinedione compound as claimed in claim 1 wherein R is chloroalkyl.

5. Imidazolidinedione compound as claimed in claim 1 wherein R represents chlorine, methyl, chloromethyl, dichloromethyl or trichloromethyl.

6. Imidazolidinedione compound as claimed in claim 1 of the formula

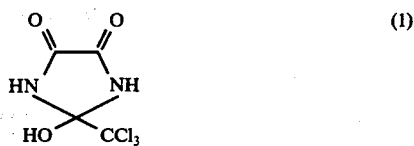
(1)

7. Imidazolidinedione compound as claimed in claim 1 of the formula

(2)

8. Plant growth regulant compositions comprising an agriculturally acceptable carrier and, in effective amounts, an imidazolidinedione compound as claimed in claim 1.

9. Method of influencing the growth of plant which method comprises applying to the plants or their habitat an effective amount of an imidazolidinedione compound as claimed in claim 1.

10. Method as claimed in claim 9 wherein the active compound is applied in an amount of from 0.01 to 50 kg per hectare.

11. Method as claimed in claim 9 wherein the active compound is applied in an amount of from 0.05 to 10 kg per hectare.

12. Method as claimed in claim 9 wherein said compound is applied in a growth inhibitingly effective dosage, to inhibit the growth of plants.

13. Method as claimed in claim 9 wherein said compound is applied in a plant growth stimulatingly effective dosage, to stimulate the growth of plants.

14. Method as claimed in claim 9 wherein said compound is applied in a plant growth altering effective dosage, to alter the growth of plants.

* * * * *